United States Patent [19]

Petraitis et al.

[11] Patent Number: 5,244,917
[45] Date of Patent: Sep. 14, 1993

[54] SUBSTITUTED NAPHTHOFURANS AS ANTI-INFLAMMATORY AGENTS

[75] Inventors: Joseph J. Petraitis, Glenmoore, Pa.; Donald J. P. Pinto, Newark, Del.

[73] Assignee: The DuPont Merck Pharmaceutical Company, Wilmington, Del.

[21] Appl. No.: 893,409

[22] Filed: Jun. 2, 1992

[51] Int. Cl.$^5$ .................. A61K 31/34; C07D 407/12
[52] U.S. Cl. .................. 514/468; 514/826; 514/886; 549/458
[58] Field of Search .......... 549/458; 514/468, 886, 514/826

[56] References Cited

U.S. PATENT DOCUMENTS

| | | | |
|---|---|---|---|
| 2,682,473 | 9/1949 | Thompson et al. | 549/458 |
| 3,965,124 | 6/1976 | Eder et al. | 549/458 |
| 4,057,562 | 11/1977 | Balli et al. | 549/458 |
| 4,470,990 | 9/1984 | Asselin et al. | 549/458 |
| 4,857,516 | 8/1989 | Terao et al. | 549/458 |
| 4,943,589 | 7/1990 | Crews et al. | 549/458 |

OTHER PUBLICATIONS

Chem. Abs. Service CA:109(25):230726q, 1988.
Chem. Abs. Service CA:91(21):175135d, 1979.
Chem. Abs. Service CA:94(19):156687f, 1980.
Makovetskii et al, Ukrainskii Khimicheskii Zhurnal, vol. 51, No. 5, pp. 528-531, 1985.
Junek et al., Monatshefte fur Chemie 99, 2359-2364 (1968).

Primary Examiner—Marianne M. Cintins
Assistant Examiner—Catherine S. Kilby Scalzo
Attorney, Agent, or Firm—Blair Q. Ferguson; Gildo E. Fato; Theresa M. Stevens

[57] ABSTRACT

This invention relates to substituted naphthofurans as anti-inflammatory and anti-allergic agents, pharmaceutical compositions containing them, processes for their preparation, and their use as anti-inflammatory and anti-allergic agents. The naphthofurans are of the formula

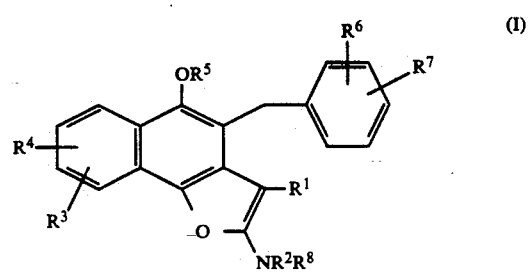

and pharmaceutically acceptable salts thereof wherein:
$R^1$ is CN or $COOR^9$;
$R^2$ and $R^8$ independently are H, $C_1$-$C_4$ alkyl, $COR^9$ or $COR^{10}$;
$R^3$, $R^4$, $R^6$ and $R^7$ are independently H, $C_1$-$C_4$ alkyl, halogen, phenyl, $CF_3$ or $OR^9$;
$R^5$ is H, $C_1$-$C_4$ alkyl, or $COR^9$; and
$R^9$ and $R^{10}$ are independently $C_1$-$C_4$ alkyl, halogen or aryl.

12 Claims, No Drawings

SUBSTITUTED NAPHTHOFURANS AS ANTI-INFLAMMATORY AGENTS

FIELD OF THE INVENTION

This invention relates to substituted naphthofurans as anti-inflammatory and anti-allergic agents, pharmaceutical compositions containing them, processes for their preparation, and their use as anti-inflammatory and anti-allergic agents.

BACKGROUND OF THE INVENTION

Inflammatory responses to offending stimuli are known to be promoted by products of arachidonic acid metabolism. These products include leukotrienes and prostaglandins. The initial step in the "arachidonic acid cascade" involves the release of arachidonic acid from phospholipids or from triglycerides. The enzymes catalyzing such release of arachidonic acid include phospholipase C and phospholipase $A_2$.

Inhibitors of phospholipase C and phospholipase $A_2$ may be valuable therapeutic agents having wide applicability in inflammatory and allergic conditions in mammals. Although some currently available anti-inflammatory agents show inhibitory activity against these enzymes of the "arachidonic acid cascade", there is a continuing need for safer and more effective agents capable of treating inflammatory and allergic diseases.

SUMMARY OF THE INVENTION

According to the present invention, there are provided naphtho[1,2-b]furans of Formula I, and pharmaceutically acceptable salts thereof, pharmaceutical compositions comprising such compounds and pharmaceutically acceptable carriers, processes for their preparation, and methods of using these compounds and compositions for the treatment of inflammatory diseases in a mammal.

This invention provides compounds of Formula (I):

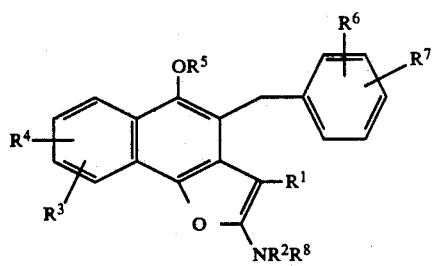

and pharmaceutically acceptable salts thereof wherein:
$R^1$ is CN or $COOR^9$;
$R^2$ and $R^8$ independently are H, $C_1$-$C_4$ alkyl, $COR^9$ or $COR^{10}$;
$R^3$, $R^4$, $R^6$ and $R^7$ independently are H, $C_1$-$C_4$ alkyl, halogen, phenyl, $CF_3$ or $OR^9$;
$R^5$ is H, $C_1$-$C_4$ alkyl, $COR^9$ or $COR^{10}$; and
$R^9$ and $R^{10}$ are independently $C_1$-$C_4$ alkyl or aryl.

Preferred compounds are those of Formula (I) in which $R^5$ is H.

More preferred compounds are those in which:
$R^1$ is CN or $CO_2CH_3$;
$R^2$ is H or $COC_2H_5$;
$R^3$ is H, 7-$OCH_3$ or 8-$OCH_3$;
$R^4$ is H, F or $CH_3$;
$R^5$ is H, F or $COC_2H_5$;
$R^7$ is H; and
$R^8$ is H or $COC_2H_5$.

Illustrative of the most preferred compounds of Formula (I) are the following:
2-amino-4-benzyl-3-cyano-5-hydroxynaphtho[1,2-b]furan;
2-amino-4-(2-fluoro)benzyl-3-cyano-5-hydroxynaphtho[1,2-b]furan;
2-amino-4-(4-fluoro)benzyl-3-cyano-5-hydroxynaphtho[1,2-b]furan;
2-amino-4-benzyl-3-cyano-5-hydroxy-8-methoxynaphtho[1,2-b]furan;
2-amino-4-benzyl-3-cyano-5-hydroxy-7-methoxynaphtho[1,2-b]furan;
2-amino-4-(2-fluoro)benzyl-3-cyano-5-hydroxy-8-methoxynaphtho[1,2-b]furan.

In the present invention it has been discovered that the compounds above are useful as inhibitors of enzymes catalyzing release of arachidonic acid, and for the treatment of inflammatory and allergic diseases.

The present invention also provides methods for the treatment of inflammatory and allergic diseases in a mammal by administering to the mammal a pharmaceutically effective amount of a compound of Formula (I) as described above.

The compounds herein described may have asymmetric centers. All chiral, diastereomeric, and racemic forms are included in the present invention. When any variable (for example, $R^9$ and $R^{10}$) occurs more than one time in any constituent or in Formula (I), or any other formula herein, its definition on each occurrence is independent of its definition at every other occurrence. Also, combinations of substituents and/or variables are permissible only if such combinations result in stable compounds. As used herein, "alkyl" is intended to include both branched and straight-chain saturated aliphatic hydrocarbon groups having the specified number of carbon atoms. "Halo" as used herein refers to fluoro, chloro, bromo, and iodo; and "counterion" is used to represent a small, negatively charged species such as chloride, bromide, hydroxide, acetate, sulfate, and the like. As used herein, "aryl" or "aromatic residue" is intended to mean phenyl or naphthyl.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in "*Remington's Pharmaceutical Sciences,*" 17th ed., p. 1418, Mack Publishing Company, Easton, Pa., (1985), the disclosure of which is hereby incorporated by reference.

DETAILED DESCRIPTION OF THE INVENTION

Synthesis

The compounds of Formula (I) may be prepared using the reactions, techniques, and general synthetic procedures described below. Each of the references cited below are hereby incorporated herein by reference. Reactions are performed in solvents appropriate to the reagents and materials employed and suitable for the transformation being effected. It is understood by those skilled in the art of organic synthesis that the functionality present on portions of the molecule must be compatible with the reagents and reaction conditions proposed.

Compounds of Formula (I), in which $R^1$ is cyano and $R^2$, $R^5$, and $R^8$ are hydrogen, may be conveniently prepared by a method similar to that outlined by H. Junek, H. Sterk and B. Hornischer, *Monatshefte fur Chemie,* 99 2359-64 (1968). Thus, reaction of malononitrile with a base, for example potassium hydride, followed by addition of a quinone of Formula (II) is carried out in an inert solvent, for example dry tetrahydrofuran, under an atmosphere of nitrogen between 0° C. and the boiling point of the solvent. Aqueous workup provides the compounds of Formula (III). This is illustrated in Scheme 1.

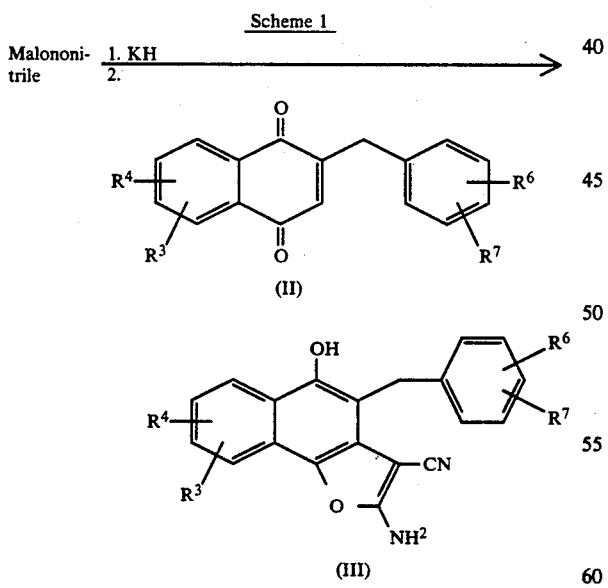

The quinons of Formula (II), if not commercially available, may be obtained from substituted naphthols of Formula (IV) upon treatment with an appropriate oxidant, for example Fremy's salt, as outlined in Fieser and Fieser, "*Reagents for Organic Synthesis,*" 1, 940-942, Wiley - Interscience, New York, (1967). This is illustrated in Scheme 2.

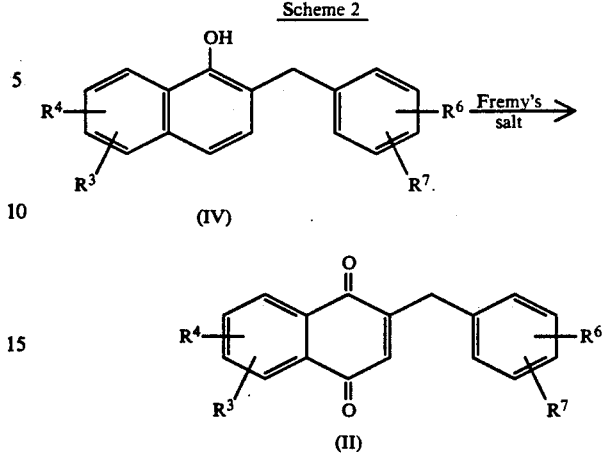

Compounds of Formula (I), in which $R^1$ is $CO_2R^9$ and $R^2$, $R^5$ and $R^8$ are hydrogen, may be conveniently prepared by a method similar to that used to prepare compounds of Formula (III). Thus, reaction of a substituted cyanoacetate of Formula (V) with a base, for example potassium hydride, followed by addition of a quinone of Formula (II) is carried out in an inert solvent, for example tetrahydrofuran, under an atmosphere of nitrogen between 0° C. and the boiling point of the solvent. Aqueous workup provides the compounds of Formula (VI). This is illustrated in Scheme 3.

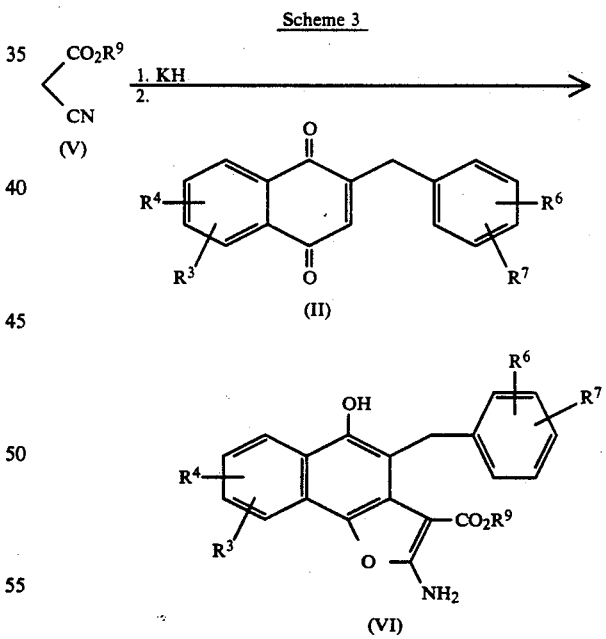

Compounds of Formula (I), in which $R^2$ is hydrogen and $R^5$ and $R^8$ are $COR^9$, may be prepared by treating a compound of Formula (VII) with an appropriately substituted anhydride of the formula $(R^9CO)_2O$ in the presence of triethylamine and a catalytic amount of 4-dimethylaminopyridine (DMAP). The reaction is carried out under an atmosphere of nitrogen in an inert solvent, for example dry tetrahydrofuran, between 0° C. and the boiling point of the solvent. Removal of solvent and subsequent chromatographic separation provides compounds of Formula (VIII). This is illustrated in Scheme 4.

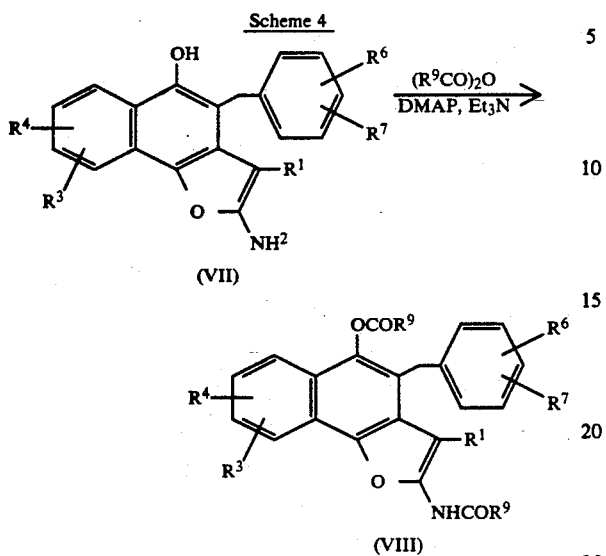

Compounds of Formula (I), in which $R^2$ and $R^5$ are hydrogen and $R^8$ is $COR^9$, may be conveniently prepared by treatment of compounds of Formula (VIII) with dilute hydroxide, for example sodium hydroxide, in water at room temperature. Neutralization with dilute acid, for example hydrochloric acid, followed by extraction and chromatographic purification provides compounds of Formula (IX). This is illustrated in Scheme 5.

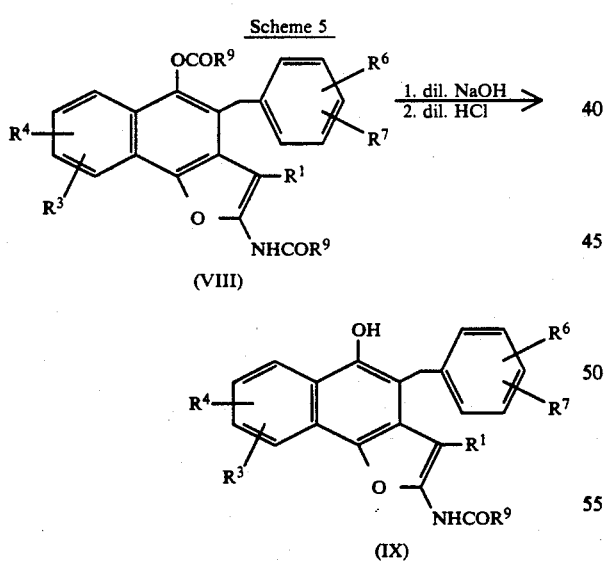

Compounds of Formula (I), in which $R^2$, $R^5$ and $R^8$ are $C_1$–$C_4$ alkyl, may be prepared by treatment of compounds of Formula (X) with base, for example anhydrous potassium carbonate, in the presence of excess $C_1$–$C_4$ alkyl iodide. The reaction is carried out an atmosphere of nitrogen in a dry solvent, for example acetone, at the boiling point of the solvent. After several hours, additional $C_1$–$C_4$ alkyl iodide is added along with dry N,N-dimethylformamide and the mixture stirred at the boiling point of the solvent overnight. Aqueous workup provides compounds of Formula (XI). This is illustrated in Scheme 6.

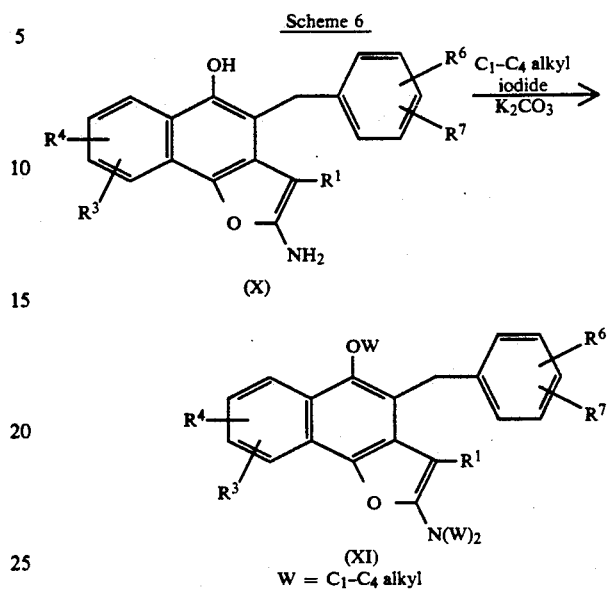

Compounds of Formula (I), in which $R^5$ is hydrogen and $R^2$ and $R^8$ are $C_1$–$C_4$ alkyl, may be prepared by treatment of compounds of Formula (XI) with potassium thiomethoxide. The reaction is carried out under an atmosphere of nitrogen in dry N,N-dimethylformamide at 140° C. Aqueous workup provides compounds of Formula (XII). This is illustrated in Scheme 7.

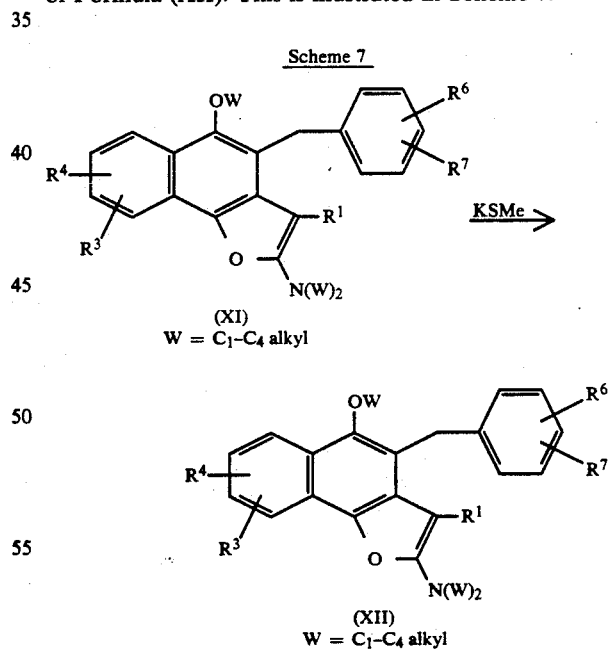

Compounds Formula (I) in which $R^2$ and $R^8$ are hydrogen, and $R^5$ is $C_1$–$C_4$ alkyl, may be prepared by treatment of compounds of Formula (X) with base, for example anhydrous potassium carbonate, and excess $C_1$–$C_4$ alkyl iodide. The reaction is carried out under an atmosphere of nitrogen in a solvent, for example dry acetone, at the boiling point of the solvent. Aqueous workup followed by chromatographic purification provides compounds of Formula (XIII). This is illustrated in Scheme 8.

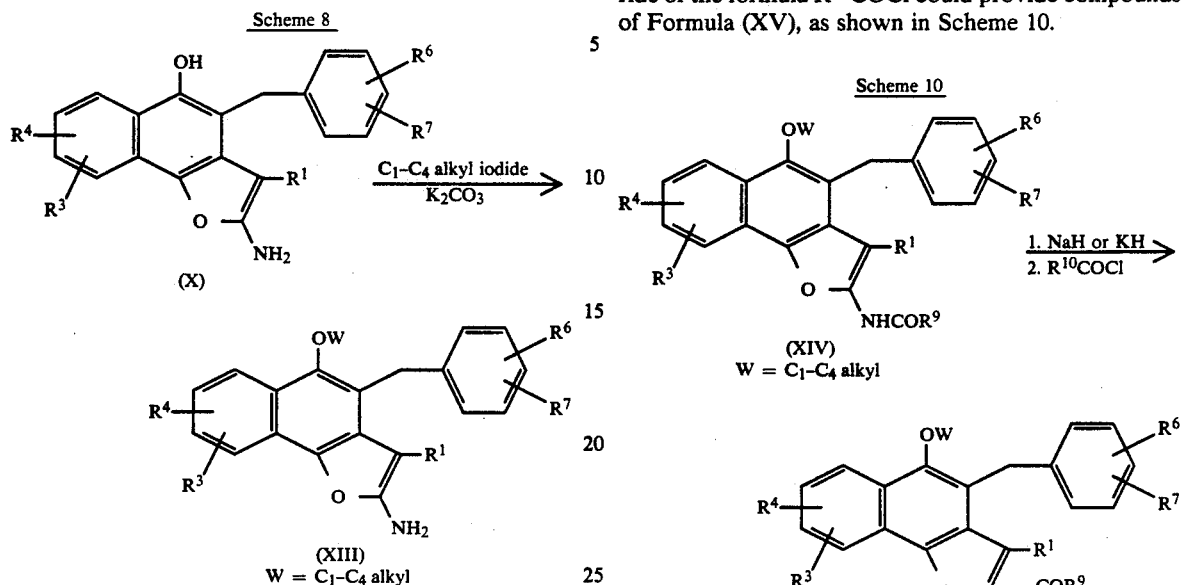

Compounds of Formula (I), in which $R^5$ is $C_1$–$C_4$ alkyl, $R^2$ ($R^8$) is hydrogen and $R^8$ ($R^2$) is $COR^9$, could be prepared from compounds of Formula (XIII) by treatment with an anhydride of the formula $(R^9CO)_2O$ in the presence of triethylamine and a catalytic amount of 4-dimethylaminopyridine. The reaction could be carried out in an inert solvent, for example dry tetrahydrofuran, under an atmosphere of nitrogen between 0° C. and the boiling point of the solvent, similar to conditions used for the preparation of compounds of Formula (VIII). Such a procedure could provide compounds of Formula (XIV) as shown in Scheme 9.

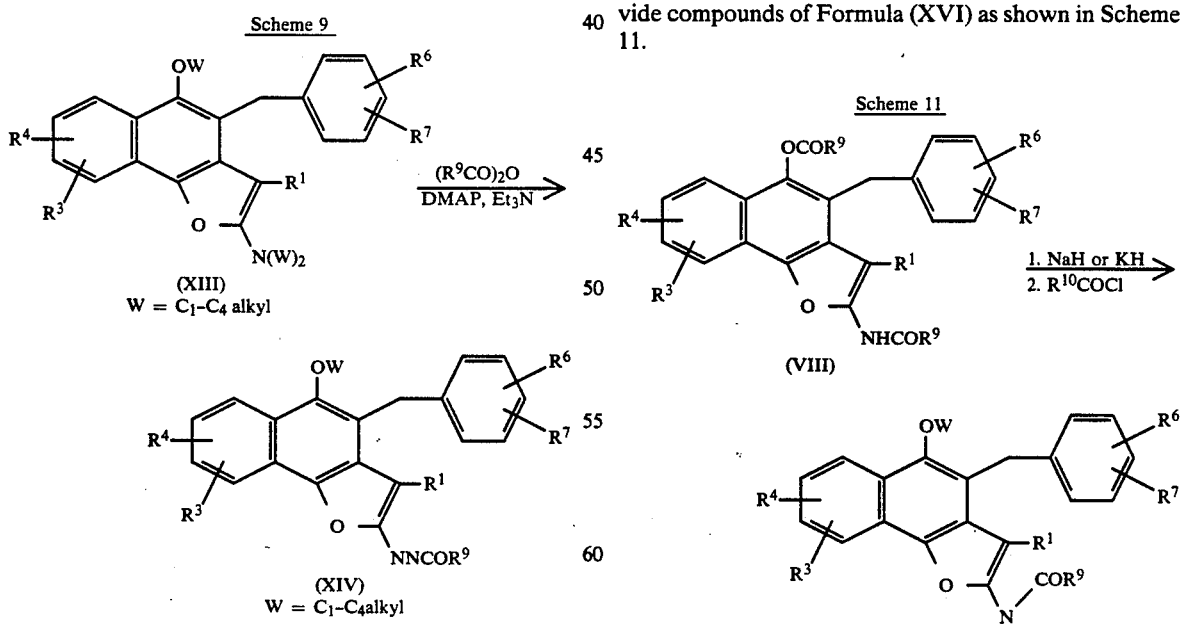

Compounds of Formula (I), in which $R^5$ is $C_1$–$C_4$ alkyl, $R^2$ ($R^8$) is $COR^9$ and $R^8$ ($R^2$) is $COR^{10}$, prepared by the general method outlined in March, "*Advanced Organic Chemistry: Reactions, Mechanisms, and Structure,*" p.340, McGraw-Hill, New York, (1968). Thus, treatment of compounds of Formula (XIV) with sodium hydride or potassium hydride followed by an acid chloride of the formula $R^{10}COCl$ could provide compounds of Formula (XV), as shown in Scheme 10.

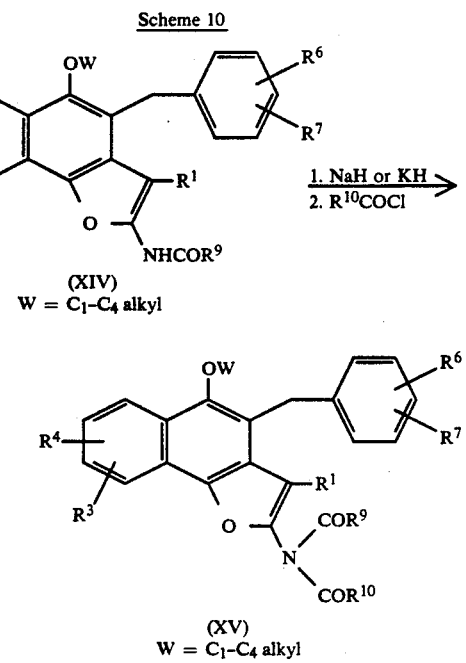

Compounds of Formula (I), in which $R^5$ is $COR^9$, $R^2$ ($R^8$) is $COR^9$ and $R^8$ ($R^2$) is $COR^{10}$ could be prepared using a method similar to that described for the preparation of compounds of Formula (XV). Thus, treatment of compounds of Formula (VIII) with a hydride, for example sodium hydride or potassium hydride, followed by an acid chloride of the formula $R^{10}COCl$ could provide compounds of Formula (XVI) as shown in Scheme 11.

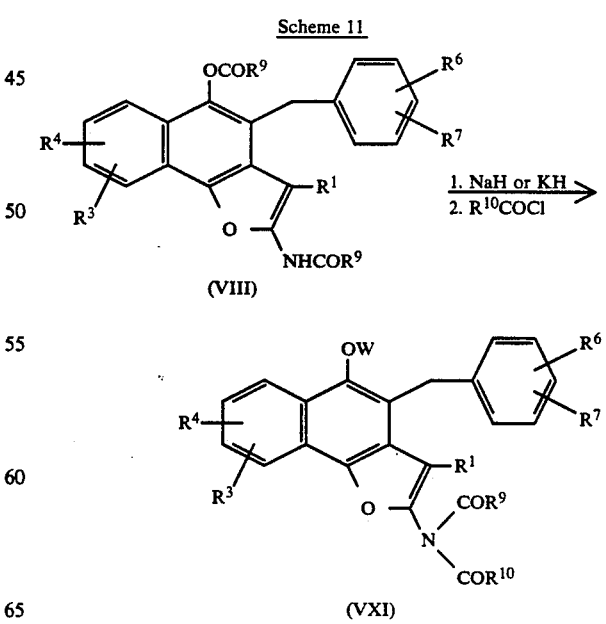

Compounds of Formula (I), in which $R^5$ is hydrogen, $R^2$ ($R^8$) is $COR^9$ and $R^8$ ($R^2$) is $COR^{10}$, could be prepared by a method similar to that described for the preparation of compounds of Formula (IX). Thus, treatment of compounds of Formula (XVI) with dilute hydroxide, for example sodium hydroxide, followed by treatment with dilute acid, for example hydrochloric acid, could provide compounds of Formula (XVII), as shown in Scheme 12.

Scheme 12

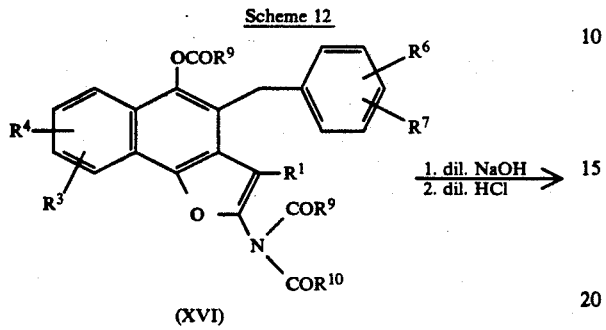

(XVI)

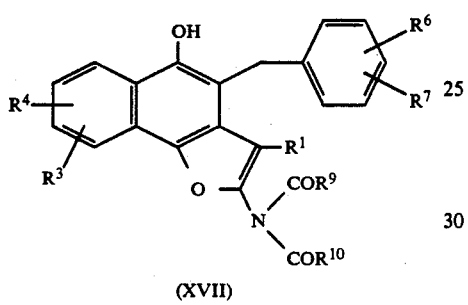

(XVII)

Compounds of Formula (I), in which $R^5$ is $COR^9$, $R^2$ ($R^8$) is $COR^{10}$ and $R^8$ ($R^2$) is hydrogen, could be prepared from compounds of Formula (IX) by treatment with an anhydride of the formula $(R^9CO)_2O$ under conditions similar to those used for the preparation of compounds of Formula (VIII). Such a procedure could result in the preparation of compounds of Formula (XVIII), as shown in Scheme 13.

Scheme 13

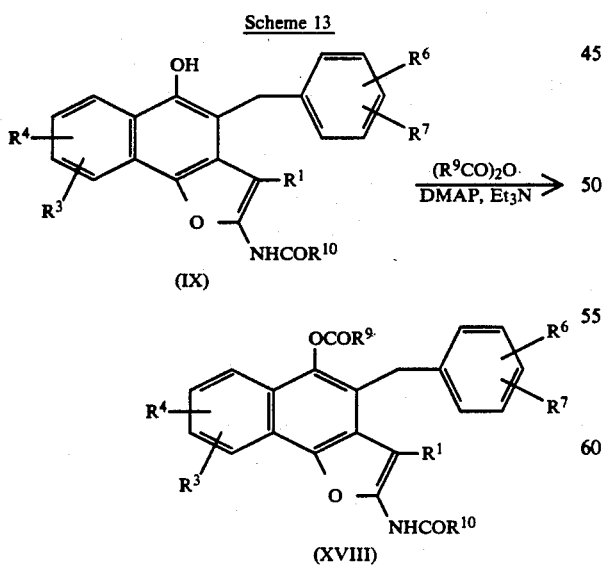

Compounds of Formula (I), in which $R^5$ is $COR^9$ and $R^2$ and $R^8$ are $C_1-C_4$ alkyl could be prepared from compounds of Formula (XII) by treatment with an anhydride of the formula $(R^9CO)_2O$ under conditions similar to those used for the preparation of compounds of Formula (VIII). Such a procedure could result in the preparation of compounds of Formula (XIX), as shown in Scheme 14.

Scheme 14

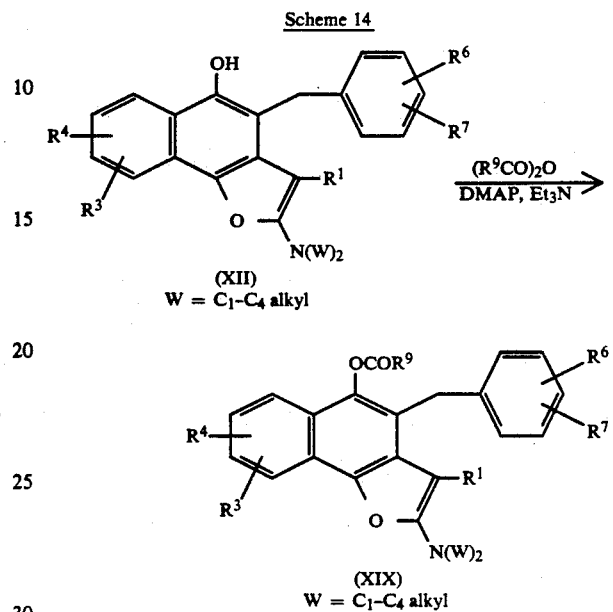

Compounds of Formula (I), in which $R^5$ is $COR^9$, $R^2$ ($R^8$) is $COR^{10}$ and $R^8$ ($R^2$) is $C_1-C_4$ alkyl, could be prepared from compounds of Formula (XVIII) by treatment with silver oxide and $C_1-C_4$ alkyl iodide similar to that procedure described by T. J. King and C. E. Newall, *J. Chem. Soc.*, 974 (1965). Such a procedure could result in the preparation of compounds of Formula (XX), as shown in Scheme 15.

Scheme 15

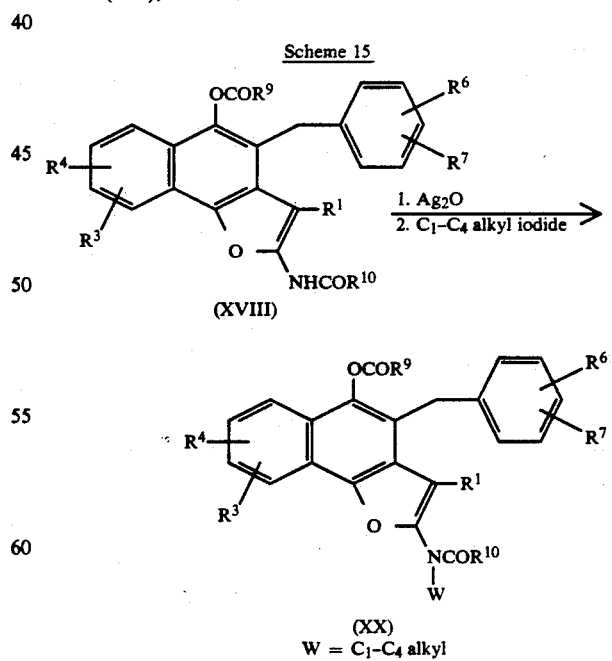

Compounds of Formula (I), in which $R^5$ is hydrogen, $R^2$ ($R^8$) is $COOR^{10}$ and $R^8$ ($R^2$) is $C_1-C_4$ alkyl, could be prepared from compounds of Formula (XX) by treatment with dilute hydroxide, for example sodium hydroxide, under conditions similar to those used for the preparation of compounds of Formula (IX). Such a procedure could result in the preparation of compounds of Formula (XXI), as shown in Scheme 16.

Scheme 16

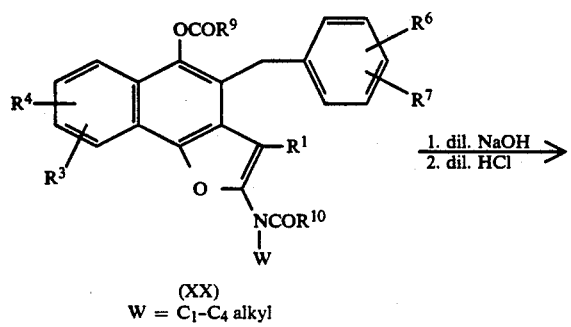

(XX)
W = C$_1$–C$_4$ alkyl

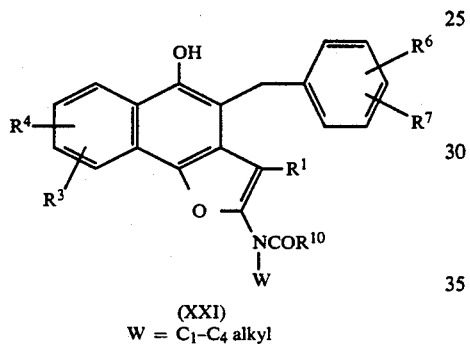

(XXI)
W = C$_1$–C$_4$ alkyl

Compounds of Formula (I), in which R$^2$ and R$^8$ are C$_1$–C$_4$ alkyl, and R$^5$ is a different C$_1$–C$_4$ alkyl could be prepared from compounds of Formula (XII) by treatment with (C$_1$–C$_4$)* alkyl iodide (in which (C$_1$–C$_4$)* denotes a different alkyl group as compared to those contained on R$^2$ and R$^8$) under conditions similar to those used for the preparation of compounds of Formula (XI). Such a procedure could result in the preparation of compounds of Formula (XXII), as shown in Scheme 17.

Scheme 17

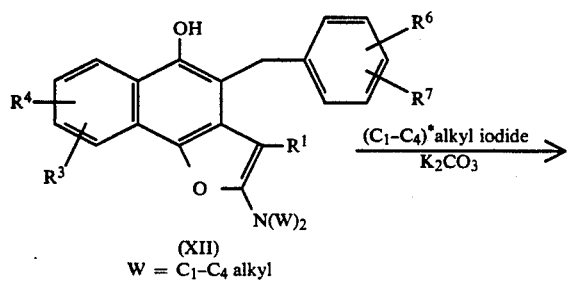

(XII)
W = C$_1$–C$_4$ alkyl

-continued
Scheme 17

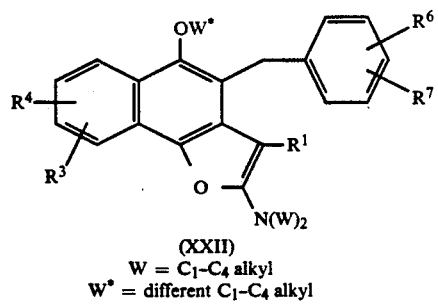

(XXII)
W = C$_1$–C$_4$ alkyl
W* = different C$_1$–C$_4$ alkyl

Compounds of Formula (I), in which R$^2$ (R$^8$) is COR$^9$, R$^8$ (R$^2$) is C$_1$–C$_4$ alkyl and R$^5$ is the same or different C$_1$–C$_4$ alkyl, could be prepared from compounds of Formula (XXI) by treatment with (C$_1$–C$_4$)* alkyl iodide under conditions similar to those used for the preparation of compounds of Formula (XI). Such a procedure could result in the preparation of compounds of Formula (XXIII), as shown in Scheme 18.

Scheme 18

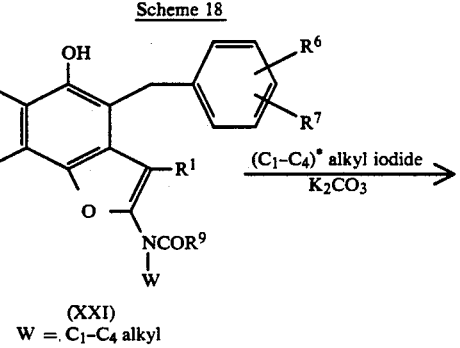

(XXI)
W = C$_1$–C$_4$ alkyl

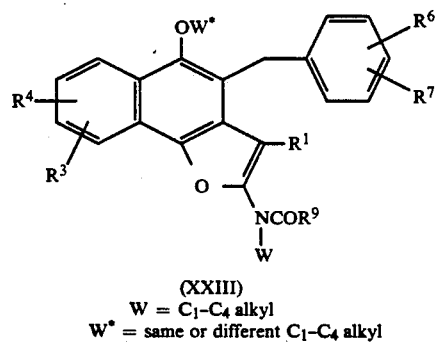

(XXIII)
W = C$_1$–C$_4$ alkyl
W* = same or different C$_1$–C$_4$ alkyl

EXAMPLES

The compounds of this invention and their preparation can be further understood by the following examples, which exemplify but do not constitute a limitation of the invention. In these examples, unless otherwise indicated, all temperatures are degrees centigrade and parts and percentages are by weight.

In the examples, $^1$H NMR spectra (δppm) were recorded in d$_6$ DMSO or CDCl$_3$ on a Varian 300 spectrometer. Infrared spectra (cm$^{-1}$) were recorded on a Perkin Elmer 1600 FT spectrometer in Nujol or KBr disk. Tetrahydrofuran was distilled from sodium benzophenone under nitrogen. Other reagents were used as sold by commercial sources. Silica gel 60 (230–400 mesh) supplied by Merck was used for flash chromatography. All examples shown in Table 1 were prepared by the general method outlined for Example 1.

EXAMPLE 1

2-Amino-4-benzyl-3-cyano-5-hydroxynaphtho[1,2-b]furan

A mixture of potassium hydride (7.56 g, 63 mmol, 35% oil dispersion) and hexane (250ml) was stirred at room temperature under nitrogen. Solvent was decanted off and substituted with dry tetrahydrofuran (250ml). Malononitrile (4.16 g, 63 mmol), dissolved in tetrahydrofuran (50 ml), was then added to the slurry dropwise. A mixture of 2-benzyl-1,4-naphthoquinone (15.62 g, 63 mmol) and tetrahydrofuran (50 ml) was then added dropwise. The reaction mixture was set at reflux for 2h, allowed to cool to room temperature and quenched with methanol (50 ml). The mixture was poured into water (100 ml) and extracted into ethyl acetate (3 x 250 ml). The organic layer was dried (magnesium sulfate) and evaporated to an oil. Chromatography (silica gel: hexane/ethyl acetate (2 : 1) as eluant) of the oily residue afforded 7.48 g (23 mmol, 38%) of product as green crystals, m.p. 224°–225 ° C.; $^1$H NMR (d$_6$ DMSO): 4.5(s,2H), 7.1–7.6 (m, 7H), 7.9(d, $^1$H), 9.25(s, $^1$H); IR (nujol): 3460, 3310, 3240, 3190, 2220; High resolution mass spectrum: calculated 314.1055, measured 314.1061.

EXAMPLE 58

2-Amino-4-benzyl-3-carbomethoxy-5-hydroxynaphtho[1,2-b]furan

The title compound was prepared by reaction of methyl cyanoacetate with 2-benzyl-1,4-naphthoquinone following the procedure outlined for example 1. Obtained as tan crystals (55%); m.p. 170°–171° C.; $^1$H NMR (CDCl$_3$): 3.66(s, 3H), 4.05(s,2H), 5.07(s,2H), 7.17–7.53(m, 8H), 7.98(d, $^1$H), 8.10(d,$^1$H); IR (nujol): 3309, 3479, 3566, 1725, 1604; Chemical ionization mass spectrum m/z (rel. intensity) 348 (M+H, 100); calculated for C$_{21}$H$_{17}$NO$_4$ C 72.61, H 4.93; measured C 72.79, H 4.68, N 4.00.

TABLE I

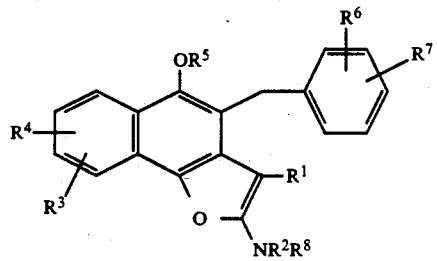

(I)

| Ex No | R$^1$ | R$^2$ | R$^3$ | R$^4$ | R$^5$ | R$^6$ | R$^7$ | R$^8$ | M.P. |
|---|---|---|---|---|---|---|---|---|---|
| 1 | CN | H | H | H | H | H | H | H | 224–225° C. |
| 2 | CN | H | H | H | H | o-F | H | H | 206–207° C. |
| 3 | CN | H | H | H | H | m-F | H | H | |
| 4 | CN | H | H | H | H | p-F | H | H | 233–235° C. |
| 5 | CN | H | H | H | H | m-Cl | H | H | |
| 6 | CN | H | H | H | H | m-Cl | p-F | H | |
| 7 | CN | H | H | H | H | o-OC$_6$H$_5$ | H | H | |
| 8 | CN | H | H | H | H | m-OC$_6$H$_5$ | H | H | 210–212° C. |
| 9 | CN | H | H | H | H | p-OC$_6$H$_5$ | H | H | 235–236° C. |
| 10 | CN | H | H | H | H | o-OCH$_3$ | p-OCH$_3$ | H | |
| 11 | CN | H | 7-OCH$_3$ | H | H | H | H | H | 226–228° C. |
| 12 | CN | H | 8-OCH$_3$ | H | H | H | H | H | 227–229° C. |
| 13 | CN | H | 9-OCH$_3$ | H | H | H | H | H | 255–257° C. |
| 14 | CN | H | 7-OCH$_3$ | H | H | o-CH$_3$ | H | H | |
| 15 | CN | H | 8-OCH$_3$ | H | p-F | H | H | H | 197–199° C. |
| 16 | CN | H | 8-OCH$_3$ | H | o-F | H | H | H | 240–241° C. |
| 17 | CN | H | 7-OCH$_3$ | H | H | o-CH$_3$ | p-CH$_3$ | H | |
| 18 | CN | H | 7-OCH$_3$ | H | H | p-C$_6$H$_5$ | H | H | |
| 19 | CN | H | 8-OCH$_3$ | H | H | p-CF$_3$ | H | H | |
| 20 | CN | H | 9-OCH$_3$ | H | H | o-Cl | H | H | |
| 21 | CN | H | 9-OCH$_3$ | H | H | o-F | p-F | H | |
| 22 | CN | H | 7-OCH$_3$ | 8-F | H | H | H | H | 238–239° C. |
| 23 | CN | H | 7-OCH$_3$ | 8-F | H | o-F | H | H | |
| 24 | CN | H | 7-OCH$_3$ | 8-F | H | p-Cl | H | H | |
| 25 | CN | H | 7-OCH$_3$ | 8-F | H | o-CH$_3$ | H | H | |
| 26 | CN | H | 7-OCH$_3$ | 8-F | H | o-CH$_3$ | p-CH$_3$ | H | |
| 27 | CN | H | 7-OCH$_3$ | 8-F | H | p-C$_6$H$_5$ | H | H | |
| 28 | CN | H | 7-OCH$_3$ | 8-F | H | p-CF$_3$ | H | H | |
| 29 | CN | H | 7-CH$_3$ | 9-CH$_3$ | H | H | H | H | 157–160° C. |
| 30 | CN | H | 7-CH$_3$ | 9-CH$_3$ | H | o-Cl | H | H | |
| 31 | CN | H | 7-CH$_3$ | 9-CH$_3$ | H | p-F | H | H | |
| 32 | CN | H | 7-CH$_3$ | 9-CH$_3$ | H | p-CF$_3$ | H | H | |
| 33 | CN | H | 7-CH$_3$ | 9-CH$_3$ | H | p-C$_6$H$_5$ | H | H | |
| 34 | CN | H | 7-CH$_3$ | 9-CH$_3$ | H | o-CH$_3$ | H | H | |
| 35 | CN | H | 7-CH$_3$ | 9-CH$_3$ | H | o-CH$_3$ | p-CH$_3$ | H | |
| 36 | CN | H | 8-OCH$_3$ | H | H | o-F | H | H | 240–242° C. |
| 37 | CN | H | 8-OCH$_3$ | H | H | p-F | H | H | 197–199° C. |
| 38 | CN | H | 8-OCH$_3$ | H | H | p-OC$_6$H$_5$ | H | H | 204–206° C. |
| 39 | CN | H | 8-OCH$_3$ | H | H | p-C$_6$H$_5$ | H | H | |
| 40 | CN | H | 8-OCH$_3$ | H | H | o-CH$_3$ | p-CH$_3$ | H | |

TABLE I-continued

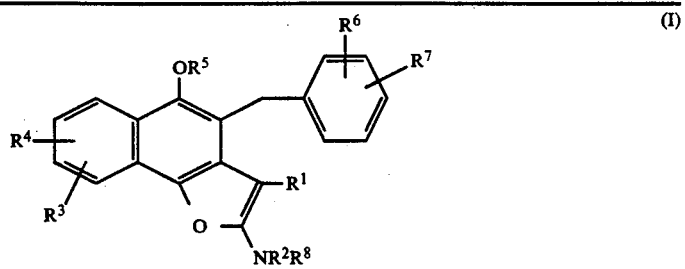

(I)

| Ex No | R¹ | R² | R³ | R⁴ | R⁵ | R⁶ | R⁷ | R⁸ | M.P. |
|---|---|---|---|---|---|---|---|---|---|
| 41 | CN | H | 8-OCH₃ | H | H | m-F | p-F | H | 234–235° C. |
| 42 | CN | CH₃ | H | H | CH₃ | H | H | H | |
| 43 | CN | CH₃ | H | H | CH₃ | H | H | CH₃ | |
| 44 | CN | CH₃ | H | H | H | H | H | CH₃ | |
| 45 | CN | CH₃ | 7-OCH₃ | H | CH₃ | H | H | CH₃ | |
| 46 | CN | CH₃ | 7-OCH₃ | H | H | H | H | CH₃ | |
| 47 | CN | CH₃ | 7-OCH₃ | H | CH₃ | CH₃ | H | CH₃ | |
| 48 | CN | CH₃ | 7-OCH₃ | H | CH₃ | p-CF₃ | H | CH₃ | |
| 49 | CN | CH₃ | 7-OCH₃ | H | H | p-CF₃ | H | CH₃ | |
| 50 | CN | CH₃ | 7-OCH₃ | 8-F | CH₃ | H | H | CH₃ | |
| 51 | CN | CH₃ | 7-OCH₃ | 8-F | H | H | H | CH₃ | |
| 52 | CN | CH₃ | 7-OCH₃ | H | CH₃ | H | H | H | |
| 53 | CN | CH₃ | 7-OCH₃ | H | CH₃ | o-Cl | H | H | |
| 54 | CN | COCH₃ | H | H | COCH₃ | H | H | COCH₃ | |
| 55 | CN | COCH₃ | H | H | COCH₃ | H | H | H | |
| 56 | CN | COCH₃ | H | H | COCH₃ | o-OCH₃ | H | COCH₃ | |
| 57 | CN | COC₂H₅ | 7-OCH₃ | 8-F | COC₂H₅ | m-F | H | COC₂H₅ | |
| 58 | CN | COC₂H₅ | 7-OCH₃ | 8-F | COC₂H₅ | p-Cl | H | COC₂H₅ | |
| 59 | CO₂CH₃ | H | H | H | H | H | H | H | 169–171° C. |
| 60 | CO₂CH₃ | H | H | H | H | m-OC₆H₅ | H | H | 172–173° C. |
| 61 | CO₂CH₃ | H | H | H | H | p-F | H | H | |
| 62 | CO₂CH₃ | H | 7-OCH₃ | H | H | p-C₆H₅ | H | H | |
| 63 | CO₂CH₃ | H | 7-OCH₃ | H | H | o-Cl | H | H | |
| 64 | CO₂CH₃ | CH₃ | H | H | CH₃ | H | H | H | |
| 65 | CO₂CH₃ | CH₃ | H | H | CH₃ | o-F | H | H | |
| 66 | CO₂CH₃ | CH₃ | H | H | CH₃ | m-Cl | p-F | H | |
| 67 | CO₂CH₃ | CH₃ | H | H | CH₃ | p-C₆H₅ | H | H | |
| 68 | CO₂CH₃ | CH₃ | 7-OCH₃ | H | CH₃ | H | H | H | |
| 69 | CO₂CH₃ | CH₃ | 7-OCH₃ | H | CH₃ | H | H | COCH₃ | |
| 70 | CO₂CH₃ | CH₃ | 7-OCH₃ | H | H | H | H | COCH₃ | |
| 71 | CO₂CH₃ | CH₃ | 7-OCH₃ | 8-F | CH₃ | o-OCH₃ | p-OCH₃ | COCH₃ | |
| 72 | CO₂CH₃ | CH₃ | 7-OCH₃ | 8-F | CH₃ | p-F | H | COCH₃ | |
| 73 | CO₂CH₃ | CH₃ | 7-OCH₃ | 8-F | CH₃ | p-F | H | H | |
| 74 | CO₂CH₃ | CH₃ | 7-OCH₃ | 8-F | H | p-C₆H₅ | H | H | |

Utility

The phospholipase A₂ and phospholipase C inhibitors of this invention can be administered to treat inflammatory and allergic conditions, including but not limited to rheumatoid arthritis and other rheumatic disorders, collagen diseases, allergic diseases, chronic obstructive and bronchospastic lung diseases such as asthma and bronchitis. The compounds of this invention may also be useful in the treatment of osteoarthritis.

A23187 Ear Edema Model

To measure anti-inflammatory activities of the investigational compounds the following standard murine ear edema protocol was used. Edema was induced by the calcium ionophore, A23187 (10 μg/ear) [Marks, F., Furstenberger, G., Kownatzki, E., Prostaglandin E Mediated Stimulation of Mouse Epidermis in vivo by Divalent Cation Ionophore A23187 and by Tumor Promotor TPA, Cancer Res., 41, 696–702 (1981)]. Male CF-1 (Charles River) 18–20 grams were used. Investigational compounds (in acetone at 100 μg/ear) were applied to one ear just prior to application of the inflammagen (A23187). Six hours after A23187 application, edema was determined by comparing the weights of 6 mm punch biopsies from control (solvent) and inflammagen-treated ears. Percent inhibition was calculated using standard equations. Results are shown in Table II below. The results show that the compounds described herein effectively suppress the mitotic activity associated with mouse skin hyperplasia induced by A23187, indicative of efficacy in treating human inflammatory diseases, including human skin and muco-epithelial diseases.

Platelet Phospholipase C Assay

Platelet phospholipase C was measured using a 100,000×g supernatant extract of platelet cells as the enzyme preparation. The assay mixture consisted of (in final concentrations): ³H myoinositol phosphatidylinositol, (200 mM, 0.1Ci), CaCl₂ (5 mM), Tris acetate buffer (60 mM, pH 4.5–7.5), sodium deoxycholate (2 mg/ml), platelet supernatant protein heated at 100° C. for 5 min (1 mg/ml), all in a total volume of 300 ml.

The assay was performed according to the method of Rittenhouse [Rittenhouse, S., Preparation of Selectively Labeled Phosphoinositol and Assay of Phosphoinositol-specific Phospholipase C in Methods in Enzymology, Lands, W. and Smith, W., eds., 86, 3–11 (1982)]. The hydrolysis of substrate to water soluble product was calculated on the basis of the specific activity of the substrate. The activity of the compounds was expressed as the percent inhibition of control (no compound) PLC hydrolysis. The results are shown in Table II below. The results show that the compounds described herein effectively inhibit PLC activity, an enzyme involved in the generation of arachidonic acid. Arachidonic acid is the precursor of inflammagens such as leukotrienes and prostaglandins which are involved in the mediation of the inflammatory process.

TABLE II

| Example No. (M) | A23187 % inhibition | PLC IC50 |
|---|---|---|
| $1 \times 10^{-5}$ | 83 | 1.5 |
| $2 \times 10^{-5}$ | 71 | 2.6 |
| $4 \times 10^{-4}$ | 58 | 1.2 |
| $11 \times 10^{-4}$ | 82 | 1.9 |
| $12 \times 10^{-5}$ | n.d. | 5.5 |
| 15 | 91 | n.d. |
| $16 \times 10^{-5}$ | n.d. | 5.6 | n.d. not determined

Dosage and Formulation

Compounds may be administered by any means that enables the active agent to reach the agent's site of action in the body of a mammal. They can be administered by any of the conventional means available for administration of pharmaceuticals, either as individual therapeutical agents or in combinations with other therapeutic agents. They can be administered alone, but are generally administered with a pharmaceutical carrier selected on the basis of the chosen route of administration and standard pharmaceutical practice.

The dosage administration will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually, a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration generally contain from about 1 milligram to about 500 milligrams of active ingredient per unit. In these pharmaceutical compositions the active ingredient will ordinarily be present in an amount of about 0.5-95 % by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions, and glycols such as propylene glycol or polyethylene glycols are suitable carriers for parenteral solutions. Solutions for parenteral administration contain the active ingredient, and, if necessary, suitable stabilizing agents, and/or buffer substances. Antioxidants such as sodium bisulfite, sodium sulfite, or ascorbic acid either alone or in combination are frequently suitable stabilizing agents. Also used are citric acid and its salts and sodium EDTA. In addition, parenteral solutions can contain preservatives, such as benzalkonium chloride, methyl and/or phenyl parabens, and chlorobutanol.

Suitable pharmaceutical carriers are described in "*Remington's Pharmaceutical Sciences,*" Mack Publishing, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules each containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by dissolving 1.5% by weight of active ingredient in a solution containing 10% by volume of propylene glycol in water. The solution is sterilized by commonly used techniques.

Suspension

An aqueous suspension is prepared for oral administration so that each 5 milliliters contains 25 milligrams of finely divided active ingredients, 200 milligrams of sodium carboxymethyl cellulose, 5 milligrams of sodium benzoate, 1.0 gram of sorbitol solution, U.S.P., and 0.025 milliliter of vanillin.

Nasal Spray

An aqueous solution is prepared such that each 1 milliliter contains 10 milligrams of active ingredient, 1.8 milligrams methylparaben, 0.2 milligram propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Compounds of this invention were tested in the following assays, representative results of which are shown in Table II.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited applications may provide further useful information these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

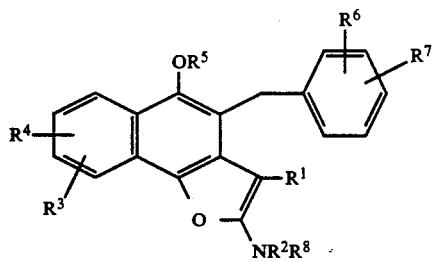

(I)

or pharmaceutically acceptable salts thereof wherein:
$R^1$ is CN or $COOR^9$;
$R^2$ and $R^8$ independently are H, $C_1$–$C_4$ alkyl, $COR^9$ or $COR^{10}$;
$R^3$, $R^4$, $R^6$ and $R^7$ are independently H, $C_1$–$C_4$ alkyl, halogen, phenyl, $CF_3$ and $OR^9$;
$R^5$ is H, $C_1$–$C_4$ alkyl, or $COR^9$; and
$R^9$ and $R^{10}$ are independently $C_1$–$C_4$ alkyl, halogen or phenyl or naphthyl, 2. A compound of claim 1 wherein $R^5$ is H.
3. A compound of claim 1 wherein
$R^1$ is CN or $CO_2CH_3$;
$R^2$ is H or $COC_2H_5$;
$R^3$ is H, 7-$OCH_3$ or 8-$OCH_3$;
$R^4$ is H, F or $CH_3$;
$R^5$ is H, F or $COC_2H_5$;
$R^7$ is H; and
$R^8$ is H or $COC_2H_5$.

4. A compound of claim 1 which is selected from the group consisting of:
2-amino-4-benzyl-3-cyano-5-hydroxynaphtho[1,2-b]furan;
2-amino-4-(2-fluoro)benzyl-3-cyano-5-hydroxynaphtho[1,2-b]furan;
2-amino-4-(4-fluoro)benzyl-3-cyano-5-hydroxynaphtho[1,2-b]furan;
2-amino-4-benzyl-3-cyano-5-hydroxy-8-methoxynaphtho[1,2-b]furan;
2-amino-4-benzyl-3-cyano-5-hydroxy-7-methoxynaphtho[1,2-b]furan;
2-amino-4-(2-fluoro)benzyl-3-cyano-5-hydroxy-8-methoxynaphtho[1,2-b]furan.

5. A pharmaceutical composition comprising an effective anti-inflammatory or anti-allergic amount of a compound of claim 1 and a pharmaceutically acceptable carrier.

6. A pharmaceutical composition comprising an effective anti-inflammatory or anti-allergic amount of a compound of claim 2 and a pharmaceutically acceptable carrier.

7. A pharmaceutical composition comprising an effective anti-inflammatory or anti-allergic amount of a compound of claim 3 and a pharmaceutically acceptable carrier.

8. A pharmaceutical composition comprising an effective anti-inflammatory or anti-allergic amount of a compound of claim 4 and a pharmaceutically acceptable carrier.

9. A method of treating inflammatory or allergic conditions in a mammal comprising administering to said mammal a therapeutically effective amount of a compound of claim 1.

10. A method of treating inflammatory or allergic conditions in a mammal comprising administering to said mammal a therapeutically effective amount of a compound of claim 2.

11. A method of treating inflammatory or allergic conditions in a mammal comprising administering to said mammal a therapeutically effective amount of a compound of claim 3.

12. A method of treating inflammatory or allergic conditions in a mammal comprising administering to said mammal a therapeutically effective amount of a compound of claim 4.

* * * * *